US012788046B2

(12) United States Patent
Mercati et al.

(10) Patent No.: US 12,788,046 B2
(45) Date of Patent: Nov. 10, 2026

(54) SYSTEM WITH EMERGING PROPERTIES FOR USE IN THE TREATMENT OF METABOLIC SYNDROME

(71) Applicant: Aboca S.p.A. Società Agricola, Sansepolcro (IT)

(72) Inventors: Valentino Mercati, Sansepolcro (IT); Francesca Marini, Sansepolcro (IT)

(73) Assignee: Aboca S.p.A. Società Agricola, Sansepolcro (IT)

( * ) Notice: Subject to any disclaimer, the term of this patent is extended or adjusted under 35 U.S.C. 154(b) by 611 days.

(21) Appl. No.: 18/042,889

(22) PCT Filed: Aug. 24, 2021

(86) PCT No.: PCT/IB2021/057750

§ 371 (c)(1),
(2) Date: Feb. 24, 2023

(87) PCT Pub. No.: WO2022/043869

PCT Pub. Date: Mar. 3, 2022

(65) Prior Publication Data

US 2023/0354869 A1 Nov. 9, 2023

(30) Foreign Application Priority Data

Aug. 26, 2020 (IT) ........................ 102020000020467

(51) Int. Cl.

| | |
|---|---|
| ***A23L 33/22*** | (2016.01) |
| ***A23L 33/105*** | (2016.01) |
| ***A23L 33/24*** | (2016.01) |
| ***A61K 36/28*** | (2006.01) |
| ***A61K 36/33*** | (2006.01) |
| ***A61K 36/55*** | (2006.01) |
| ***A61K 36/899*** | (2006.01) |
| ***A61P 3/00*** | (2006.01) |

(52) U.S. Cl.

CPC ............. *A23L 33/22* (2016.08); *A23L 33/105* (2016.08); *A23L 33/24* (2016.08); *A61K 36/28* (2013.01); *A61K 36/33* (2013.01); *A61K 36/55* (2013.01); *A61K 36/899* (2013.01); *A61P 3/00* (2018.01)

(58) Field of Classification Search

None

See application file for complete search history.

(56) References Cited

FOREIGN PATENT DOCUMENTS

| | | | |
|---|---|---|---|
| EP | 1679009 | A1 | 7/2006 |
| WO | WO-2014007635 | A1 | 1/2014 |

OTHER PUBLICATIONS

Liu, Health-Promoting Components in Fruits and Vegeatbles in the Diet, 2013, J American Society for Nutrition Adv Nutr, 4: 3845-3925.*

Bensadon, S., et al., "By-products of Opuntia ficus-indica as a source of antioxidant dietary fiber," Plant Foods for Human Nutrition 65(3):210-216, Kluwer Academic Publishers, Switzerland (2010).

De Santiago, E., et al., "Impact of cooking process on nutritional composition and antioxidants of cactus cladodes (Opuntia ficus-indica)," Food Chemistry 240:1055-1062, Elsevier, Netherlands (2017).

Ibrahim Abd El-Moaty, H., et al., "Structural elucidation of phenolic compounds isolated from Opuntia littoralis and their antidiabetic, antimicrobial, and cytotoxic activity," South African Journal of Botany 131:320-327, Elsevier, Netherlands (2020).

International Search Report and Written Opinion for International Application No. PCT/IB2021/057750, European Patent Office, Netherlands, 20 pages.

Mannai, F., et al., "Cellulosic fibers from lignocellulosic biomass for papermaking applications," Chapter 8 in *Food Preservation and Waste Exploitation*, Socaci, S.A., et al., eds., InTech Open, United Kingdom (2019).

Stagi, S., et al., "Retrospective Evaluation of Metformin and/or Metformin Plus a New Polysaccharide Complex in Treating Severe Hyperinsulinism and Insulin Resistance in Obese Children and Adolescents with Metabolic Syndrome," Nutrients 9(5):524, MDPI, Switzerland (2017).

* cited by examiner

*Primary Examiner* — Anand U Desai
*Assistant Examiner* — Catheryne Chen
(74) *Attorney, Agent, or Firm* — STERNE, KESSLER, GOLDSTEIN & FOX P.L.L.C.

(57) ABSTRACT

The present invention provides a new system with emerging properties in the form of a mixture or composition and the use of the same in the treatment or in assisting the treatment of the metabolic syndrome or one or more symptoms related to it.

12 Claims, 3 Drawing Sheets

SYSTEM WITH EMERGING PROPERTIES FOR USE IN THE TREATMENT OF METABOLIC SYNDROME

Figure 1:
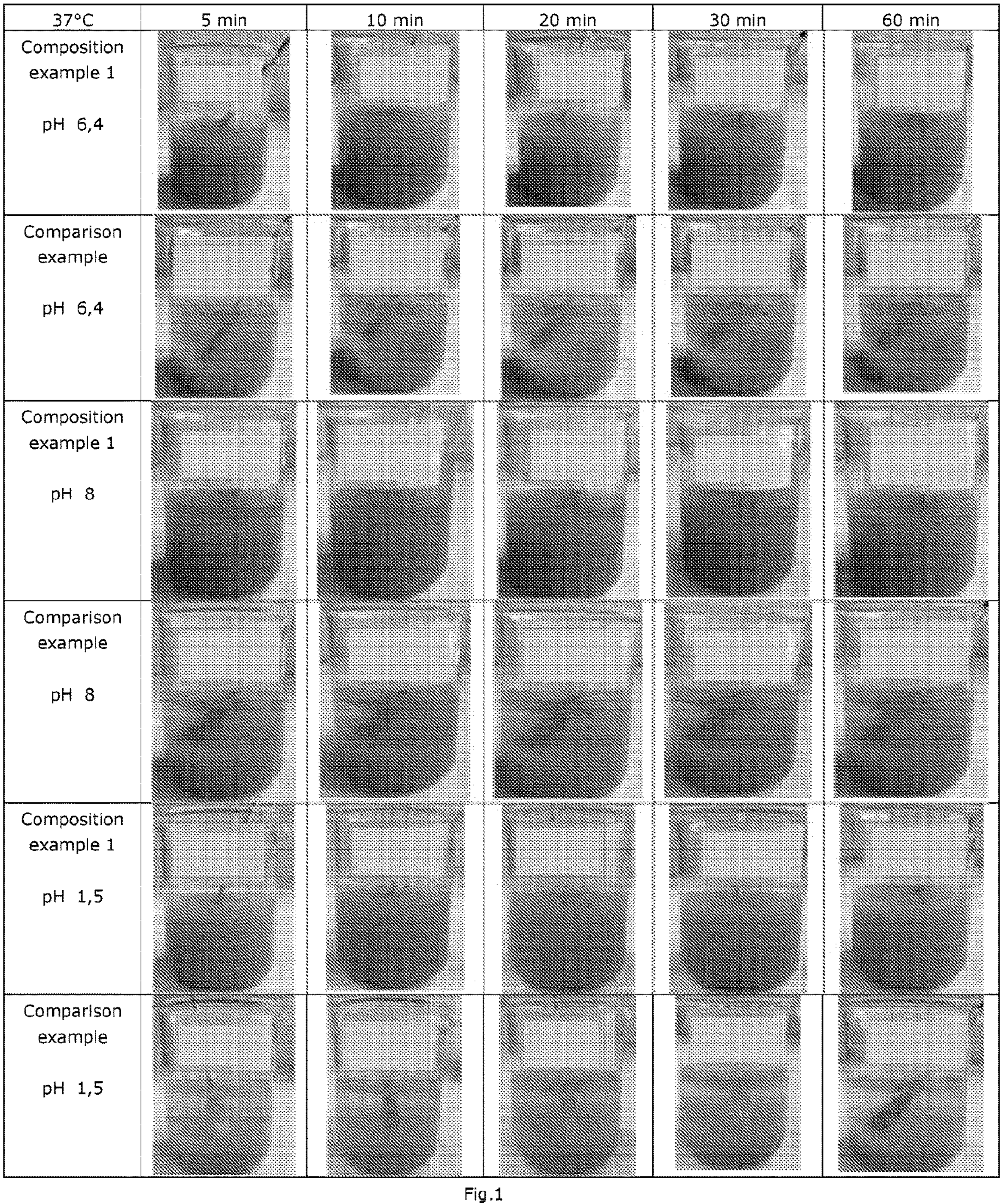

The present invention provides a new system with emerging properties in the form of a mixture or composition and the use of the same in the treatment or in assisting the treatment of the metabolic syndrome or one or more related symptoms.

STATE OF THE ART

The metabolic syndrome is a set of metabolic alterations associated with visceral obesity; these alterations include insulin resistance, hypertension, dyslipidemia (hypertriglyceridemia, low HDL levels), as well as visceral obesity.

This pathological condition is accurately defined in "The IDF consensus worldwide definition of the metabolic syndrome published in 2006 by the International Diabetes Federation (IDF)". This condition is diagnosed on the basis of the presence of a high abdominal circumference associated with at least two of the alterations described in this publication and reported in the glossary below and determines increased risk factors for cardiovascular, hepatic and pancreatic decompensation. These metabolic imbalances are linked to the onset of insulin resistance which causes real alterations in many organs and tissues of the body but is mainly the cause of atherosclerosis, hepatic steatosis and reduction of beta cells in the pancreas. This helps to explain why the metabolic syndrome is strongly correlated with an increased risk of incurring cardiovascular disease and type II diabetes which are among the main causes of death in the Western population. Recent data indicate that this syndrome affects 10-40% of the population with a variability that depends on ethnicity, age, lifestyle (diet, physical activity). In this context it is useful to underline that in recent years there has been a significant increase in this syndrome, an increase determined by the increase in calorie intake, by the increased consumption of foods with a higher energy density, with high levels of saturated fats and sugar but poor in nutrients, reduced physical activity, all conditions that have led to an increase in the frequency of obesity, and in particular of the high abdominal circumference (index of metabolic imbalances) considered today a real epidemic. According to data from the World Health Organization, in 2016 more than 1.9 billion adults (over 18 years of age) were overweight (BMI ≥25); of these, 650 million were obese (BMI>30). These data expressed as a percentage describe the world population in this way: about 13% of adults (11% of men and 15% of women) in 2016 were obese, while 39% (39% of men and 40% of women) was overweight. Additionally, in 2016, approximately 41 million children under the age of 5 were estimated to be overweight or obese, and 340 million children and adolescents (ages 5-19 years) were overweight or obese. Child obesity is also often characterized by an increase in visceral fat, insulin resistance and is associated with predictor markers of type 2 diabetes and metabolic syndrome. A 2006 Italian study involving children from Southern Italy reported that 40.8% of obese children and 41.2% of obese adolescents had HOMA values indicative of insulin resistance (>2.5 and >4.0 respectively) while only 3.0% of normal-weight children and/or normal-weight adolescents had HOMA values indicative of insulin resistance (p<0.0001 and p<0.002, respectively). It is therefore clear that an obese child has a greater risk of becoming an obese adult the greater the degree of obesity; therefore, prevention and treatment interventions must be set up before adolescence, also taking into account the greater difficulty in making an obese teenager lose weight permanently, due to a series of biological and psychosocial constraints.

Metabolic syndrome is therefore a multifactorial condition that is difficult to treat because the most effective therapy is that which acts on lifestyles (diet and physical activity) but has low compliance. In general, in addition to behavioural advice, we tend to treat individual metabolic imbalances such as e.g. dysglycaemia with metformin, dyslipidemia with statins and fibrates, hypertension with antihypertensives and it is easy to conclude that this approach is unsuccessful because it not only does not treat the problem in its complexity but also leads to further iatrogenic disorders and diseases caused by polypharmacy. It is also well known that polytherapy is paradoxically associated with a therapeutic failure often resulting from poor adherence to a complex treatment, increased side effects, inappropriate prescription, poor doctor-patient communication and poor patient education (Volpe, M., G. Pignatelli and F. Paneni. "Polytherapy in cardiovascular prevention: Open problems." Italian Journal of Cardiology 13 (2012): 503-510) According to what reported by the IDF, the different treatments for the individual components of the metabolic syndrome include, e.g.: the treatment of atherogenic dyslipidemia with the aim of lowering TG as well as lowering ApoB and non-HDL cholesterol levels, raising HDL-c levels, reducing LDL-c levels, for example by administering fibrates (alpha PPAR agonists), statins or combinations thereof which may be complicated by side effects;

- the treatment of high blood pressure, for example with angiotensin converting enzyme inhibitors or angiotensin receptor blockers;
- the treatment of insulin resistance and hyperglycemia for which metformin, thyiazolinedione, acarbose, etc. are used The polytherapy approach is not recommended in younger subjects whose metabolic imbalances are substantially linked to weight. In this context, drug therapy and rapid weight loss are considered extreme interventions that can be used in cases of highly obese children, BMI>2 units at the 95th percentile, older than 12 years and resistant to 1 year of dietary and behavioural treatment, who have marked abdominal adiposity, impaired glucose tolerance or insulin resistance, hepatic steatosis and hyperandrogenism, respiratory disorders, etc.

Various drugs or compositions are reported in the literature that show efficacy in the treatment or in assisting the treatment of one or more symptoms related to the metabolic syndrome. Among the products based on substances of natural origin, a polysaccharide complex based on cellulose, hemicellulose, pectin and mucilage is reported (Stagi et al 2017 "Retrospective Evaluation of Metformin and/or Metformin Plus a New Polysaccharide Complex in Treating Severe Hyperinsulinism and Insulin Resistance in Obese Children and Adolescents with Metabolic Syndrome"; and Stagi et al 2015 "Policaptil Gel Retard significantly reduces body mass index and hyperinsulinism and may decrease the risk of type 2 diabetes mellitus (T2DM) in obese children and adolescents with family history of obesity and T2DM "Ital J Pediatr. 2015 Feb. 15; 41:10. doi: 10.1186/s13052-015-0109-7) which, associated with drugs and/or a suitable lifestyle and diet, further reduces BMI and insulin resistance thus favouring a general metabolic recovery. The data reported in the literature show the possibility of a different approach from the polytherapy approach in the treatment of the metabolic syndrome.

The very high number of cases of metabolic syndrome and the constant decrease in the average age of the onset of this pathological condition, underlines the urgency to identify new compositions, preferably based on natural active substances and therefore not synthetic for therapy or to assist the therapy of the metabolic syndrome, bringing, in fact, one or more of the pathological alterations related to it to normal parameters.

SUMMARY OF THE INVENTION

The present invention provides a system with emerging properties, represented by a mixture of classes of substances that, as a whole, represents a system of active substances, for the treatment of the metabolic syndrome, or as an adjuvant in the treatment of the metabolic syndrome, which contrasts the aforementioned multifactorial pathological condition with a systemic approach, acting effectively and synchronously on all etiopathogenetic factors such as:

counteracting excessive and/or incorrect nutrition (too rich in calories and nutrients that cause glycemic and lipemic peaks that are difficult to manage by the liver), as it decreases the sense of hunger and slows down and reduces the absorption of lipids and carbohydrates.

Counteracting the unbalanced microbiota (which promotes systemic inflammation, the accumulation of fat and hepatic steatosis), as it makes the intestinal contents more physiological, reducing excessive abdominal circumference (which causes hepatic steatosis and systemic inflammation due to dysglycaemia and dyslipidemia), as it allows the body's metabolic rebalancing.

The system of the invention, presented here in the form of a mixture or composition, acts to rebalance the metabolic management of the entire organism exclusively through physiological actions.

Advantageously, therefore, unlike the current polytherapy approach, in which each clinical manifestation that contributes to the pathology is treated individually, the system of the present invention allows a systemic (global) approach that simultaneously entails therapeutic effects on various factors contributing to the metabolic syndrome. By therapeutic effects it is meant that the system (mixture or composition) of the invention is able, with an appropriate administration and dosage regimen, to improve or assist in the improvement of one or more, at least two, preferably at least three, of the altered parameters associated with the metabolic syndrome.

Furthermore, the mixture or composition of the invention does not cause side effects at the metabolic level because it acts in harmony with the physiology of the organism by exploiting its mechanisms in its favour.

As mentioned above, traditional therapy instead acts symptomatically by forcibly adjusting every single unbalanced parameter but in turn generating new imbalances that worsen the syndrome and lead to the onset of new diseases.

Furthermore, the composition of the invention is 100% environmentally friendly and biodegradable and its use does not cause environmental pollution unlike drugs whose components can accumulate in the environment and in water, contaminating the food chain.

Thanks to the set of all the components described and claimed, the mixture or composition according to the present invention constitutes an Active Physiological System (APS), i.e. a complex system which, when placed in contact with water, is structured by forces of various nature helping to form, with its own kinetics, a homogeneous gel system. The system of the present invention, as reported in the examples section and in the figures, has a starting reduced viscosity, but it structures in a few minutes and lasts for a few hours. The result is a homogeneous system that behaves as such even if placed at acid pH, pH close to neutrality or basic pH, typical of the various segments of the gastrointestinal tract (see examples). This system therefore has a particular ergonomics as it maintains its homogeneity within the gastrointestinal tract, the ability to adapt to the entire tract and to mix with the food bolus despite the pH variations characteristic of these compartments.

This promotes interaction with the intestine in all its components (kilo, microbiota, intestinal epithelium). In fact, the APS interacts with the intestinal content (kilo), causes the change in physical properties (increase in viscosity) and dilutes the concentration of fats and carbohydrates. In particular, APS:

Thanks to the characteristic viscosity=>it makes the absorption of these substances more gradual (retard effect), while also reducing the total amount absorbed;

Thanks to the characteristic viscosity=>it normalizes the intestinal transit, further promoting the elimination of fats (cholesterol and triglycerides) and carbohydrates (including glucose); it follows a rebalancing of the intestinal flora, useful for a more rapid and stable improvement of metabolic functions;

Thanks to the characteristic three-dimensional structure=>it reduces the reabsorption of bile acids helping to rebalance the levels of circulating cholesterol and, thanks to its viscosity, it interposes between the intestinal content (rich in fats as well as any irritants) and the mucosa, favouring its protection.

All the above favours a better use of nutrients by the liver, promoting the reorganization of blood sugar, cholesterol, triglyceridemia and a decrease in abdominal circumference. The stability of the product system is confirmed by rheological studies and fractionation/separation tests using physical methods reported in the examples section, which highlight the ability of the gel to resist the induced deformation stresses, while maintaining its structure and homogeneity. This feature is particularly useful in gastrointestinal transit in which the product is subjected to compression and stress by peristaltic stimuli.

Therefore, the object of the present invention is:

A mixture comprising from 56% to 84% w/w of dietary fibers, wherein from 31% to 47% w/w of said mixture is represented by soluble fibers and from 25% to 37% w/w of said mixture is represented by insoluble fibers; vegetable fats from 0.28% to 0.42% w/w; vegetable phenols from 0.08% to 0.16% w/w; vegetable terpenes from 0.52% to 0.78% w/w; vegetable sugars from 1.62% to 2.70% w/w; water from 6.2% to 9.3%; inorganic compounds of vegetable origin, from 3.6% to 5.7% w/w; nitrogenous substances of vegetable origin from 1.84% to 2.76% w/w.

According to the invention, all the constituents of the aforementioned mixture (excluding water) are of vegetable origin. The nitrogenous substances are essentially represented by proteins and amino acids.

The mixture can therefore also be defined as a mixture comprising from 56% to 84% w/w of vegetable dietary fibers, wherein from 31% to 47% w/w of said mixture is represented by soluble fibers and from 25% to 37% w/w of said mixture is represented by insoluble fibers; vegetable fats from 0.28% to 0.42% w/w; vegetable phenols from 0.08% to 0.16% w/w; plant terpenes from 0.52% to 0.78% w/w; vegetable sugars from 1.62% to 2.70% w/w; water from 6.2% to 9.3%; inorganic compounds such as salts and/or esters of acids and/or macroelements, of vegetable origin, from 3.6% to 5.7% w/w; nitrogenous substances of vegetable origin such as mainly proteins and amino acids from 1.84% to 2.76% w/w.

A composition comprising the mixture according to any of the embodiments provided in the present description and at least one excipient and/or carrier and/or pharmaceutically acceptable natural flavour or food grade in which said mixture constitutes the active principle of said composition.

The mixture or composition according to any one of the embodiments provided in the present description for use in the treatment or in assisting in the treatment of the metabolic syndrome.

GLOSSARY

The term metabolic syndrome in the present invention is to be understood as defined in The IDF consensus worldwide definition of the metabolic syndrome published in 2006 by the International Diabetes Federation.

The aforementioned publication provides the worldwide definition of metabolic syndrome to be used in clinical practice based on a combination of parameters as reported below:

The New Definition of the International Federation for Diabetes (IDF):

| According to the new definition of the IDF, a person, to be defined as having a metabolic syndrome must have: Central obesity (defined as waist circumference * with specific values related to ethnicity) and at least any two of the following four factors: | |
|---|---|
| high triglycerides | triglycerides ≥150 mg/dL (1.7 mmol/L) or specific treatment for this lipid abnormality |
| Reduced HDL cholesterol | <40 mg/dL (1.03 mmol/L) in males <50 mg/dL (1.29 mmol/L) in females or specific treatment for this lipid abnormality |
| High blood pressure | Systolic BP ≥130 or Diasystolic BP ≥85 mmHg or treatment for previously diagnosed hypertension |
| Elevated fasting plasma glucose levels | (FPG) = 100 mg/dL (5.6 mmol/L) or previously diagnosed type 2 diabetes OGTT is strongly recommended if above 5.6 mmol/L or 100 mg/dl but not necessary to define the presence of the syndrome |

* If BMI is >30 kg/m$^2$, central obesity can be assumed and waist circumference need not be measured.

| COUNTRY/ETHNIC GROUP | | Abdominal circumference |
|---|---|---|
| Europides * In the United States, ATP III (102 cm man; 88 cm woman) they are likely to continue to be used for clinical purposes | Man | ≥94 cm |
| | Woman | ≥80 cm |
| South Asia Based on Chinese, Malay, and Asian-Indian population | Man | ≥90 cm |
| | Woman | ≥80 cm |
| Chinese | Man | ≥90 cm |
| | Woman | ≥80 cm |
| Japanese ** | Man | ≥90 cm |
| | Woman | ≥80 cm |
| Ethnic Americans from South and Central America | | Use recommendations for South Asia until more specific data becomes available |
| Sub-Saharan Africans | | Use recommendations for Europeans until more specific data becomes available |
| Populations of the East and Middle East (Arabs) | | Use recommendations for Europeans until more specific data becomes available |

* In future epidemiological studies on populations of European origin, prevalence should be given using both European and North American cut-points to allow for better comparisons.

** Different values were originally proposed for Japanese, but new data supports the use of the above values.

Other parameters related to the metabolic syndrome are an abnormal distribution of abdominal fat, atherogenic dyslipidemia, dysglycaemia, insulin resistance, vascular dysregulation, proinflammatory states, prothrombotic states, hormonal factors.

The term Central (abdominal) obesity, according to the present invention, has the meaning commonly used in medical practice. This condition can be easily evaluated using the waist circumference according to parameters known to the skilled in the art, for example following the table above. This condition, independently associated with each of the other components of the metabolic syndrome including insulin resistance, is a prerequisite risk factor for the diagnosis of the syndrome as defined by the IDF 2006. Insulin resistance, which is difficult to measure in practice daily clinic, it is not indicated as an essential requirement.

The term atherogenic dyslipidemia describes the combination of high triglycerides (TG) and low concentrations of HDL-c along with elevated apolipoprotein B (ApoB), small and dense LDL particles and small HDL particles, all of which are independently atherogenic. It is commonly seen in people with type 2 diabetes and metabolic syndrome.

Low HDL-c and high TG levels are often found associated with insulin resistance, with or without type 2 diabetes, and both are risk factors for coronary artery disease (CHD). The term Macroelements in the present description has the meaning commonly understood in the nutritional field and therefore refers to those elements present in the human body in relatively high quantities, whose daily requirement is greater than 100 mg. This category includes calcium, chlorine, phosphorus, magnesium, potassium, sodium and sulphur (also called trace elements).

The term vegetable dietary fiber according to the present invention is that commonly used in the state of the art.

In particular, the term dietary fiber includes the remaining skeleton of the cell wall of plants, resistant to digestive enzymes of the human kit, modified cellulose, plant gums, lignin and all types of polysaccharides that are not digestible by humans.

Physiological definition: "dietary fiber is the dietary component resistant to degradation by the enzymes of the enzymatic kit."

Chemical definition: "dietary fiber is the sum of polysaccharides of non-starch origin and lignin."

Dietary fibers are present in many plants such as: oat bran, pearl barley, legumes, potatoes, dried fruit, apricot, apple, brown rice.

In the present invention, the term vegetable dietary fiber refers to the set of dietary fibers present in one or more plants and not to individual fibers purified by them, such as for example microcrystalline cellulose or the like.

The term "system with emerging properties" refers, in the present description, to a system, in this case a mixture or a composition, which exhibits an emergent behaviour, that is, the agents that make up the mixture, operating in a specific environment, (in this case in the digestive system) give rise to more complex behaviours as a system. The properties themselves are not easily predictable, and represent a subsequent level of evolution of the system. Complex emergent behaviours are not properties of individual entities and cannot be easily recognized or inferred from the behaviour of lower-level entities.

DETAILED DESCRIPTION OF THE FIGURES

FIG. 1 shows the macroscopic evaluation of the gel formation kinetics at different pHs in three buffer systems according to USP: phosphate buffer pH 6.4 and pH 8 and chloride buffer pH 1.5. 2.5 g of example of composition 1 and 2.35 g of comparison example were dispersed in 150 ml of liquid medium and the dispersion was mixed slowly for 1 minute after which it was placed in a small bath heated to 37 °C. The macroscopic evaluation of the gel formation kinetics shows how the gel formed by the composition example 1, unlike the comparison example, is stable in the presence of a high ionic strength and a strongly acidic pH, at a pH close to neutrality as well as at basic pH, it is much more homogeneous and therefore favours the ergonomics of the system.

Figure 2:
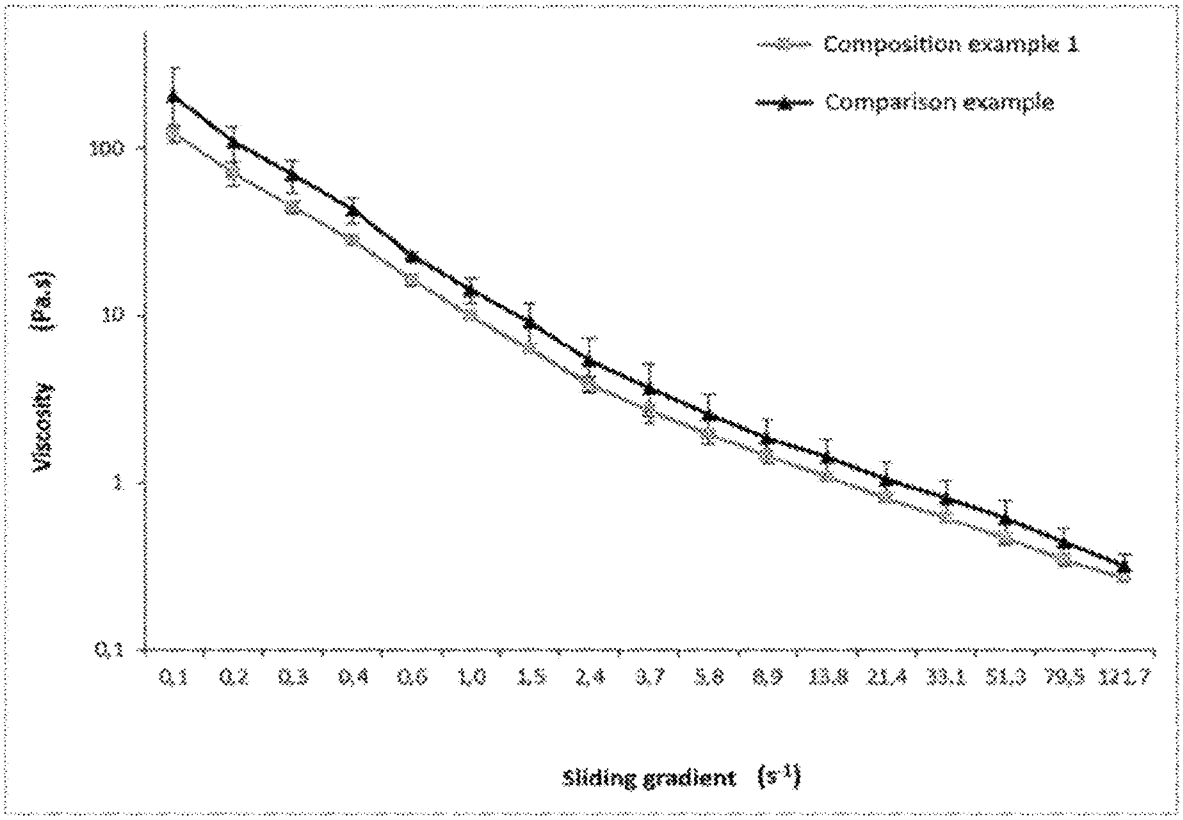

FIG. 2: flow curve of the APS sample composition example 1 and comparison example subjected to 0.1-100 s slip gradient.

Figure 3:
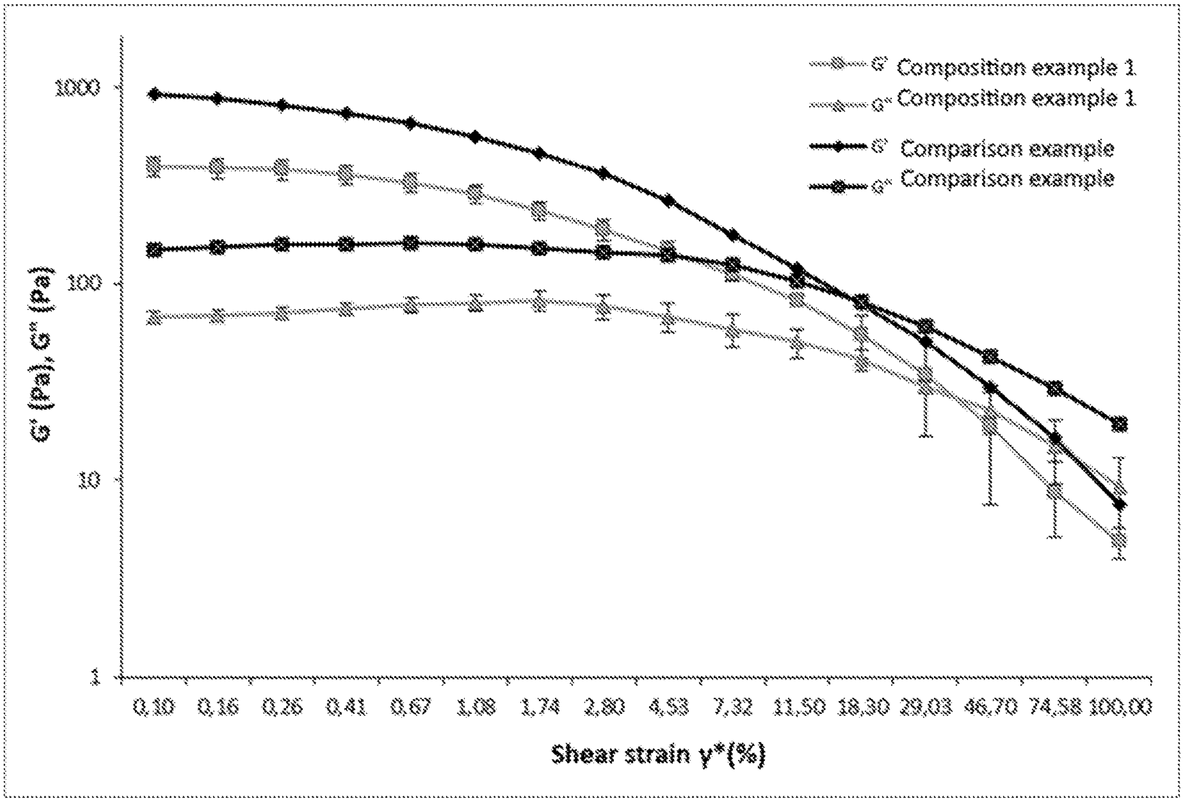

FIG. 3: determination of the Linear Visco-Elastic Region (LVER), the elastic modulus (G') and the viscous modulus (G").

DETAILED DESCRIPTION

The present invention therefore relates to a system with emergent properties in the form of a mixture comprising from 56% to 84% w/w of dietary fibers, wherein from 31% to 47% w/w of said mixture is represented by soluble fibers and from 25% to 37% w/w of said mixture is represented by insoluble fibers; vegetable fats from 0.28% to 0.42% w/w; vegetable phenols from 0.08% to 0.16% w/w; vegetable terpenes from 0.52% to 0.78% w/w; vegetable sugars from 1.62% to 2.70% w/w; water from 6.2% to 9.3%; inorganic compounds of vegetable origin, from 3.6% to 5.7% w/w; nitrogenous substances of vegetable origin from 1.84% to 2.76% w/w.

This system, which can be formulated by adding one or more of suitable excipients and/or carriers and/or natural food grade or pharmaceutically acceptable flavours, is indicated for the treatment or to assist in the treatment of the metabolic syndrome.

Thanks to the combination of all the components of its formulation (soluble fibers, insoluble fibers and terpenes) it constitutes an Active Physiological System (APS) which acts by interacting with the intestine in all its components (kilo, microbiota, intestinal epithelium). APS complexes with the intestinal content (kilo), causes the change in physical properties (increase in viscosity), and dilutes the concentration of fats and carbohydrates. In particular, APS:

makes the absorption of these substances more gradual (retard effect), while also reducing the total amount absorbed;

rebalances the intestinal flora, useful for a more rapid and stable improvement of metabolic functions; normalizing intestinal transit, which further promotes the elimination of fats (cholesterol and triglycerides) and carbohydrates (including glucose);

reduces the reabsorption of bile acids helping to rebalance the levels of circulating cholesterol and, thanks to its viscosity, it interposes between the intestinal content (rich in fats as well as any irritants) and the mucosa, favouring its protection.

In the system of the present invention, the soluble and insoluble vegetable fibers lead to the formation of a natural gel with physiological effects that occur along the entire length of the gastrointestinal tract which improve its transit and increase the sense of satiety due to the slowing of emptying. gastric.

The high capacity to absorb water (wbc or water binding capacity) of the soluble fibers causes the formation of the gel which causes a decrease in the absorption of nutrients, such as carbohydrates and lipids and cholesterol.

With this mechanism, a control of the postprandial glycaemic and lipemic peak is obtained, which over time leads to the improvement of the metabolic parameters of sugars and fats.

Insoluble fibers function above all as agents capable of increasing faecal mass, increasing its total weight and speeding up its expulsion with a consequent decrease in the absorption of nutrients, especially lipids.

Both for obesity/high abdominal circumference and for the recovery of dysglycaemia and dyslipidemia constituting the metabolic syndrome, it is necessary to reduce the "active" presence and bioavailability to the absorption of lipids and carbohydrates and avoid post-prandial glycaemic peaks. Both of these effects are the result due to the specific mixture of soluble and insoluble fibers contained in the system (mixture or composition) of the invention: the sequestering effect and a greater peristalsis, which promotes the elimination with the faeces of lipids and carbohydrates and any other related substances.

Both conditions require products with chemical and physical characteristics which are:

The ability to become viscous, linked to the presence of fibers

The ability to bind and retain water, expressed by the water binding capacity.

The water binding capacity (≥20% for the system of the invention) represents the ability of a fiber to swell in contact with water and keep the water itself inside its matrix even when subjected to physical stress such as centrifugation.

The mechanism of action of the system of the invention derives from said features, and can be summarized in four fundamental points:

thickening of the unmixed layer, i.e. the formation of an inert mass inside the stomach and intestine, which covers the intestinal mucosa and partially masks the nutrients in the path that lipids and carbohydrates must travel from the intestinal lumen to the enterocytes, lengthening their absorption times, and reducing and/or making the absorption of these substances more gradual (retard effect), increase in viscosity of intestinal contents with consequent contrast to the mixing of nutrients with digestive enzymes and therefore loss of digestion efficiency and consequent lower absorption of digested nutrients, adsorption and sequestration of bile acids with consequent decrease in the emulsion of lipids within the intestinal lumen, decrease in the digestive efficiency of gastric and pancreatic lipases; the sequestering effect of the water-soluble fibers of the bile salts prevents their intestinal absorption, directing the liver to a greater use of cholesterol for the new production of bile acids, generating a net reduction in the value of total cholesterol, LDL in the blood protection of the intestinal mucosa and microbiota from contact with too high concentrations of lipids and carbohydrates.

This modulated action, typical of fibers, is also typical of the mechanical action mechanism, as it does not act on specific enzymes or receptors present in the intestinal lumen, but it works on the rheological properties of the kilo and the nutrients themselves.

The more the nutrients are concentrated, due to an excessive intake, the more they interact with the fibers; the less they are concentrated, the less the intervention of the fibers on the rheological characteristics of the kilo and absorption will be incisive. Among the known critical performance parameters are the WBC and the amount of total fibers. The increase in the total volume of the intestinal content, precisely in the aqueous part, where hydrophilic nutrients and lipid micelles are dissolved, together with digestive enzymes, depends on them thereby diluting the concentration of nutrients and reducing and slowing their absorption.

In other words, the particular mixture of soluble and insoluble fibers and of the other components of the system of the invention causes, upon contact with water, the production of a viscous gel with a high level of WBC.

The authors of the present invention have surprisingly found that a careful selection of the components, wherein at least 30% of said insoluble dietary fiber is α-cellulose and at least 15% of said insoluble dietary fiber is lignin, or wherein at least the 35% of said insoluble dietary fiber is α-cellulose and at least 17% of said insoluble dietary fiber is lignin, or wherein at least 40% of said dietary fiber is α-cellulose and at least 18% of said insoluble dietary fiber is lignin, allows to obtain a system whose interaction with the water present in the alimentary duct develops a gel resistant to pH variations, which is stable at values ranging from pH 1.5 up to pH 8 values (see examples section). Said stability guarantees system compliance in all parts of the digestive system, from stomach to intestine. Furthermore, the system of the invention behaves like a pseudoplastic fluid, so that its viscosity decreases as the deformation rate increases (see section examples and figures) with a decreasing viscosity from about 123 Pa·s to 0.1 s−1, to 0.3 Pa·s at 100 s−1 at 37 °C. These viscosity values demonstrate the slow gel formation which results in a high ergonomy in the gastrointestinal tract, allowing effective mixing with the contents of the gastrointestinal tract.

The oscillatory tests carried out, and reported in the examples section, also surprisingly show, given the high lignin component of the insoluble fibers (which by its nature should counteract the formation of the gel and poorly hydrate) that the product has a broad LVER (Visco Region Linear elastic), which confirms the stability of the product.

Finally, the fractionation experiments show that the system of the present invention resists to separation while maintaining the gel structure despite the shear, pressure and temperature forces used, demonstrating the ability of the gel derived from the interaction of the system with water, to resist the induced deformation stresses, maintaining its structure and homogeneity. This feature is particularly useful in the gastrointestinal transit in which the product is subject to compression and stress by peristaltic stimuli.

Comparative tests with an analogous composition in which the insoluble fibers do not have the percentages of alpha cellulose and lignin of the mixture or of the composition according to the present description or the claims, show how relevant feature for a better effectiveness of the product in the gastrointestinal tract, are surprisingly improved, thereby allowing to obtain a more effective effect in the treatment or in adjuvating the treatment of the metabolic syndrome.

In a preferred embodiment, the present invention therefore relates to In a preferred embodiment, the present invention therefore relates to a mixture comprising from 56%. to 84% w/w of dietary fibers, of which from 31% to 47% w/w of said mixture is represented by soluble fibers and the 25% to 37% w/w of said mixture is represented by insoluble fibers; vegetable fats from 0.28% to 0.42% w/w; vegetable phenols from 0.08% to 0.16% w/w; plant terpenes from 0.52% to 0.78% w/w; vegetable sugars from 1.62% to 2.70% w/w; water from 6.2% to 9.3%; inorganic compounds such as salts and/or esters of acids and/or macroelements, of vegetable origin, from 3.6% to 5.7% w/w; nitrogenous substances of vegetable origin such as mainly proteins and amino acids from 1.84% to 2.76% w/w.

In a preferred embodiment, the present invention therefore relates to In a preferred embodiment, the present invention therefore relates to a mixture comprising from 56% to 84% w/w of dietary fibers, of which from 31% to 47% w/w of said mixture is represented by soluble fibers and the 25% to 37% w/w of said mixture is represented by insoluble fibers; vegetable fats from 0.28% to 0.42% w/w; vegetable phenols from 0.08% to 0.16% w/w; plant terpenes from 0.52% to 0.78% w/w; vegetable sugars from 1.62% to 2.70% w/w; water from 6.2% to 9.3%; inorganic compounds such as salts and/or esters of acids and/or macroelements, of vegetable origin, from 3.6% to 5.7% w/w; nitrogenous substances of vegetable origin such as mainly proteins and amino acids from 1.84% to 2.76% w/w.

In a preferred embodiment, said dietary fibers are from 59.7% to 80.8% w/w of vegetable fibers, wherein from 33.2% 3.2% to 45% w/w of said mixture is represented by soluble fibers and from 26.5% to 35.8% w/w of said mixture is represented by insoluble fibers or wherein said dietary fibers are from 63% to 77% w/w of vegetable fibers, wherein from 35% to 43% w/w of said mixture is represented by soluble fibers and from 28% to 34% w/w of said mixture is represented by insoluble fibers.

The embodiment wherein at least the 30% of said dietary insoluble fibers is α-cellulose and at least the 15% of said dietary insoluble fibers is lignin or wherein at least the 35% of said dietary insoluble fibers is α-cellulose and at least the 17% of said dietary insoluble fibers is lignin, or wherein at least the 40% of said dietary insoluble fibers is α-cellulose and at least the 18% of said dietary insoluble fibers is lignin is particularly preferred due to the advantageous effects disclosed in the example section.

In a particularly preferred embodiment about 42% of said dietary fibers is α-cellulose circa il 19% said insoluble dietary fibers is lignin.

According to the present invention, in any embodiment described or claimed both of mixture and of composition, said dietary fibers are at least two of: dietary fibers of hemp, cotton, bamboo, konjac, glucomannan, oat, spelt, rice, corn, wheat, barley, baobab, carrot, opuntia, daikon, citrus albedo, *stevia*, linden, linen, althea, mallow, acacia, xanthan gum, Larch, *Cyamopsis tetragonoloba*, sterculia, *ceratonia*, topinambur, pea, soy, *psyllium*, dandelion, chicory, amaranth, agave, karkadè, Aloe vera and are present inside said mixture in the form of flours, powders and/or aqueous or hydroalcoholic extracts.

Additionally, the mixture or the composition of the invention may comprise inulin, glucomannan and fibers in the form of vegetable gums, such as gum arabic, xanthan gum, larch gum, comma karaya.

The fibers indicated above can be found in hemp (plant), cotton (plant, cotton wool, seeds), bamboo (plant), oats (plant, seeds, cuticle), spelled (plant, seeds, cuticle), rice (plant, seeds, cuticle), corn (plant, seeds, cuticle), wheat (plant, seeds, cuticle), barley (plant, seeds, cuticle), baobab (fruit), carrot (root), konjac (tuber), opuntia (pale, fruits), daikon (horseradish) (root), citrus albedo, *stevia* (leaves, plant), linden (flowers and bracts), flax (seeds), marshmallow (root), mallow (leaves), acacia (gum arabic) (fruits, seeds, leaves), xanthan gum, Larch (gum larch), *Cyamopsis tetragonoloba* (guar gum) (buds, leaves, fruits), sterculia (karaya gum), *ceratonia* (carob, seeds), Jerusalem artichoke (root), pea (plant, fruits), soy (seeds, cuticle) *psyllium* (seeds), dandelion (root), chicory (root), amaranth (leaves), agave (plant), karkadè (leaves, flowers, seeds), Aloe vera (plant, leaves).

Preferably, in any embodiment described or claimed herein, the mixture or the composition of the invention does not comprise cellulose in microcrystalline form, in other words, the cellulose component is substantially comprised in vegetable flours or powders, and not as a substance purified therefrom.

The same applies to the lignin component.

According to the present invention, the soluble fibers can be derived from: aqueous extracts of the fibers listed above or from flours of the fruits, plants and parts of plants listed above.

As stated above, insoluble fibers can be derived from: grinding or pulverizing the plants listed below:

- hemp (plant), cotton (plant, cotton wool, seeds), bamboo (plant), oats (plant, seeds, cuticle), opuntia (shovels, fruits), spelled (plant, seeds, cuticle), rice (plant, seeds, cuticle), corn (plant, seeds, cuticle), wheat (plant, seeds, cuticle), barley (plant, seeds, cuticle), baobab (fruit), citrus albedo, *stevia* (leaves, plant), *ceratonia* (carob, seeds), pea (plant, fruits, cuticle), soy (seeds, cuticle), agave (plant).

In the present invention, opuntia can be in any embodiment opuntia *ficus* indica.

Therefore, in a preferred form, the mixture or composition of the invention comprise insoluble fibers in the form of ground or pulverized plants of the plants indicated above or of their parts (as indicated in the brackets).

The indication "plant" in brackets indicates that the ground or powder is preferably produced from the whole plant and not from individual parts of the same.

According to the present invention, the phenols can be derived from: extracts of plants containing dietary fibers and from the plant powders used. Such phenols are therefore preferably comprised in the powders and/or ground and/or in the extracts of the plants indicated above.

Terpenes can be derived from one or more of the plants listed above. In a preferred embodiment, the terpenes contained in the mixture or composition of the invention are mainly provided by *stevia*, which can be present in them, for example in the form of powder.

The nitrogenous substances according to the present invention are also contained in the extracts of plants containing dietary fiber and in the powders or ground of the plants used.

In a particular embodiment, the total fibers of the mixture or composition of the invention are glucomannan fibers from konjac, marshmallow, flax, lime, oats, *stevia*, opuntia, and also comprise inulin and gum arabic Of which soluble fibers of glucomannan, marshmallow, flax, linden, inulin, gum arabic and insoluble fibers of oats, *stevia*, opuntia Nitrogen compounds are provided by glucomannan, marshmallow, flax, lime, oat, *stevia*, opuntia, inulin, gum arabic, phenolic compounds from marshmallow, flax, lime, *stevia*, opuntia and to a lesser extent by all the powders used, sugars and derivatives from marshmallow, flax, lime, *stevia*, opuntia and to a lesser extent from all the powders used and the terpenes substantially from *stevia.*

In a preferred embodiment, the mixture or composition of the invention comprises or consists of

| CLASSES OF SUBSTANCES | Range of percentages with respect to the total weight of the mixture or composition |
|---|---|
| Nitrogen substances of vegetable origin | 1.84-2.76 |
| Total vegetable dietary fibers divided into | 56.20-84.30 |
| Total soluble fibers | 31.28-46.92 |
| Total insoluble fibers | 24.92-37.38 |
| Fats | 0.28-0.42 |
| Water | 6.20-9.30 |
| Phenols | 0.08-0.16 |
| Terpenes | 0.52-0.78 |
| Sugars | 1.62-2.7 |
| Inorganic compounds such as salts and/or esters of acids and/or macroelements, of vegetable origin | 3.6-5.7 |

The term "comprises" is used throughout the description and in the claims, when referring to the total composition of the mixture, due to the fact minimum percentages of other substances, for a total of maximum 0.5%, 1% or 2% could be present and be not detected or detectable.

In one embodiment, the mixture or composition of the invention comprises or consists of

| CLASSES OF SUBSTANCES | Range of percentages with respect to the total weight of the mixture or composition | | |
|---|---|---|---|
| | Example 1 | Example 2 | Example 3 |
| Nitrogen substances of vegetable origin | 2.20 | 2.40 | 2.30 |
| Total vegetable dietary fibers divided into | 70.00 | 70.50 | 70.25 |
| Total soluble fibers | 37.30 | 40.90 | 39.10 |
| Total insoluble fibers | 32.70 | 29.60 | 31.15 |
| Fats | 0.30 | 0.40 | 0.35 |
| Water | 7.50 | 8.00 | 7.75 |
| Phenols | 0.14 | 0.10 | 0.12 |
| Terpenes | 0.61 | 0.69 | 0.65 |
| Sugars | 1.71 | 2.60 | 2.16 |
| Inorganic compounds such as salts and/or esters of acids and/or macroelements, of vegetable origin | 4.97 | 4.46 | 4.7 |

| Component | % w/w |
|---|---|
| Glucomannan flour | 26.64-40.04 |
| Oat fiber | 24.96-37.44 |
| Opuntia | 17.55-26.33 |
| Inulin | 3.78-5.68 |
| Gum arabic powder | 3.78-5.68 |
| Impalpable stevia powder | 1.81-2.71 |
| Linden flowers and bracts mucilage extract | 0.48-0.72 |

-continued

| Component | % w/w |
|---|---|
| Flax seeds mucilage freeze-dried extract | 0.48-0.72 |
| Marshmallow root mucilage freeze-dried extract | 0.48-0.72 |
| Total | 100 |

The invention also relates to a composition comprising the mixture according to any of the embodiments provided in the present description and at least one excipient and/or carrier and/or pharmaceutically acceptable natural flavor in which said mixture constitutes the active ingredient of said composition.

According to an embodiment, the composition corresponds, as classes of substances and relative percentages, to any of the embodiments of the mixture of the invention disclosed in the present description.

Examples of composition are provided below

General Composition Example

| Component | % w/w |
|---|---|
| Glucomannan flour | 24.8-37.2 |
| Oat fiber | 23.22-34.82 |
| Opuntia | 16.32-24.48 |
| Natural flavours | 5.6-8.4 |
| Inulin | 3.52-5.58 |
| Gum arabic powder | 3.52-5.58 |
| Impalpable stevia powder | 1.68-2.52 |
| Linden flowers and bracts mucilage extract | 0.45-0.67 |
| Flax seeds mucilage freeze-dried extract | 0.45-0.67 |
| Marshmallow root mucilage freeze-dried extract | 0.45-0.67 |
| Total | 100 |

Composition Example 1

| Component | % w/w |
|---|---|
| Glucomannan flour | 31 |
| Oat fiber | 29.02 |
| Opuntia | 20.4 |
| Natural flavours | 7 |
| Inulin | 4.4 |
| Gum arabic powder | 4.4 |
| Impalpable stevia powder | 2.1 |
| Linden flowers and bracts mucilage extract | 0.56 |
| Flax seeds mucilage freeze-dried extract | 0.56 |
| Marshmallow root mucilage freeze-dried extract | 0.56 |
| Total | 100 |

Composition Example 2

| Component | % w/w |
|---|---|
| Glucomannan flour | 24.81 |
| Oat fiber | 34.82 |
| Opuntia | 24.48 |
| Natural flavours | 5.6 |
| Inulin | 3.52 |
| Gum arabic powder | 3.52 |
| Impalpable stevia powder | 1.68 |
| Linden flowers and bracts mucilage extract | 0.67 |
| Flax seeds mucilage freeze-dried extract | 0.45 |
| Marshmallow root mucilage freeze-dried extract | 0.45 |
| Total | 100 |

Composition Example 3

| Component | % w/w |
|---|---|
| Glucomannan flour | 36.59 |
| Oat fiber | 23.22 |
| Opuntia | 16.32 |
| Natural flavours | 8.4 |
| Inulin | 5.58 |
| Gum arabic powder | 5.58 |
| Impalpable stevia powder | 2.52 |
| Linden flowers and bracts mucilage extract | 0.45 |
| Flax seeds mucilage freeze-dried extract | 0.67 |
| Marshmallow root mucilage freeze-dried extract | 0.67 |
| Total | 100 |

Composition Example 4

| Component | % w/w |
|---|---|
| Glucomannan flour | 36.59 |
| Insoluble rice fiber | 23.22 |
| Opuntia | 16.32 |
| Natural flavours | 8.4 |
| Inulin | 5.58 |
| Gum arabic powder | 5.58 |
| Impalpable stevia powder | 2.52 |
| Linden flowers and bracts mucilage extract | 0.45 |
| Flax seeds mucilage freeze-dried extract | 0.67 |
| Marshmallow root mucilage freeze-dried extract | 0.67 |
| Total | 100 |

Composition Example 5

| Component | % w/w |
|---|---|
| Glucomannan flour | 36.59 |
| Insoluble rice fiber | 23.22 |
| Opuntia | 16.32 |
| Natural flavours | 8.4 |
| Inulin | 5.58 |
| Gum arabic powder | 5.58 |
| Impalpable stevia powder | 2.52 |
| Linden flowers and bracts mucilage extract | 0.45 |
| Flax seeds mucilage freeze-dried extract | 0.67 |
| Marshmallow root mucilage freeze-dried extract | 0.67 |
| Total | 100 |

The composition according to the invention can be supplied with powder, in the form of granules in sachets, tablets, capsules.

The system of the invention (mixture or composition), in any of the embodiments provided in the present description and in the claims, is indicated for the restoration or to assist in the restoration of one or more of the main index parameters of a metabolic imbalance, when these are altered.

These parameters are: (for this part it will be necessary to provide data within 12 months)

- LDL cholesterol levels ≥100 mg/dl and/or HDL cholesterol <40 mg/dl in males and <50 mg/dl in females;
- triglyceride levels ≥150 mg/dl;
- fasting glucose levels >100 mg/dl (IFG) and/or impaired glucose tolerance (or impaired glucose tolerance) 140-199 mg/dl (IGT);
- high abdominal circumference values even in subjects of normal weight (≥94 cm in males and ≥80 cm in females).

The composition of the invention can for example be administered in a daily dosage which can go for example from a minimum of 3 g to a maximum of 5 g, for example 3;

3.5; 4; 4.4; 5 g preferably divided into two administrations of, for example 1.5; 2; 2.25; 2.5 g each adminstered before main meals.

Each dose to be ingested before meals can be formulated as a single dose such as granules sachet, tablet or capsule.

The invention also relates to a mixture or composition according to any of the embodiments provided in the present description and in the claims, for use in the treatment or as an adjuvant in the treatment of the metabolic syndrome.

The treatment comprises taking the mixture or composition of the invention before main meals, for example 30', 20', 15', 10' before main meals.

If the composition is in the form of granules, in the case of suspension of the same in water or liquid, it must be ingested before the formation of the gel following contact with the liquid.

An example of dosage: 4-5 g per day for both adults and children from 8 years of age before the two main meals.

Although the first improvements occur already after the first month of therapy, it is advisable to take the product for at least 2-3 months. However, it is possible to repeat the treatment cycle several times throughout the year.

The mixture or composition is therefore preferably administered before the main meals. When the granulate is used, it can be administered in suspension in water or other liquid, shaken and ingested as soon as it is mixed, before the gel is formed, in an appropriate quantity and for an appropriate time, depending on the specific condition, starting from a few weeks until chronic intake.

At any point in the description and in the claims the term comprising may be replaced by the term "consisting of".

The examples reported below show the chemical and physical characteristics of the mixture of the invention that demonstrate its emerging properties.

The data of the experiments reported below are the results obtained using the composition shown in the composition example 1, the other composition examples provided in this description gave similar results (data not shown).

The comparative data provided are obtained using a composition in which oat fiber has been replaced with microcrystalline cellulose.

EXAMPLES

1. Product Preparation

The components of the product according to the composition examples provided are powders with defined granulometry, prepared starting from the different parts of the plants such as flowers, fruits, roots, seeds, leaves etc. using techniques known to experts in the field such as hulling, cutting, washing, blowing, sieving, drying, grinding and calibration (for example for the preparation of oat fiber and glucomannan flour), or extracts obtained by keeping the selected and cut parts of the plants in solvent, such as water or mixtures of water and alcohol, for varying times, drug/solvent ratios and temperatures. Once concentrated and pasteurized, the extracts can undergo drying or intermediate steps of centrifugation, filtration and adsorption on substrates of various kinds to standardize their content before being dried.

The product contains three aqueous extracts, in particular Altea, Linden and linseed.

The diagrams below show, by way of example, the production process of marshmallow root extract, lime extract and linseed extract.

The comparison composition is represented by composition 1 in which the oat fiber has been replaced by crystalline microcellulose.

The components of the product according to the composition examples provided in the detailed description in the form of powders or dry extracts were weighed, physically mixed and were subjected to wet granulation in order to increase the density and workability of the system.

The following examples show the data obtained with the composition example 1 provided in the detailed description.

All the components of the APS when placed in water interact through forces of various kinds, contributing to form a homogeneous product system with its own kinetics. This system is a gel that initially has a reduced viscosity, but structures over time, from a few minutes to several hours. The result is a homogeneous system that behaves as such even if placed at acid pH, pH close to neutrality or basic pH typical of the various segments of the gastrointestinal tract.

This system therefore has a particular ergonomics as it maintains its homogeneity within the gastrointestinal tract, the ability to adapt to the entire tract and to mix with the food bolus.

In order to study the physiological behaviour, experiments of suspension of the product at different pH times and of rheological characterization were carried out.

2. Study at Different pHs

To evaluate the gel formation at different pHs, three buffer systems according to USP were prepared: chloride buffer pH 1.5, phosphate buffer pH 6.4 and pH 8. 2.5 g of example of composition 1 and 2.35 g of example of comparison 2 were dispersed in 150 ml of liquid medium and the dispersion was mixed slowly for 1 minute after which it was placed in a small bath heated to 37 °C. The macroscopic evaluation of the gel formation kinetics shows how the gel formed by the composition example 1, unlike the comparison example, is stable in the presence of a high ionic strength and strongly acid pH, at pH close to neutrality as well as at basic pH, it is much more homogeneous and therefore favors the ergonomics of the system.

3. Rheological Characterization

Rheology is the study of the flow and deformation of matter. In rheometers the sample undergoes a shear deformation, i.e. it is squeezed between two surfaces. The lower surface in contact with a part of the instrument that remains stationary, the upper surface in contact with a surface that moves with a certain force which will cause, depending on the type of material (solid or liquid), or a deformation (x) which can be a function of time or if the material is a liquid everything will be rotated with a certain speed (v). This deformation X or the velocity V applies to the first layer of material, the one directly in contact with the moving surface of the rheometer. The layer of material immediately below will be dragged from the top but the deformation will be less and the v will be less. This will also apply to the immediately lower layer and so on up to the lowest layer which is instead stationary: it does not undergo any deformation or does not move at any speed. So whether the upper layer is only moved or is put in continuous movement, there is a GRADIENT. In rheometers, however, the reasoning is not in terms of force, speed, displacement. All these parameters are rescaled as a function of the sample size.

For example, F is divided by the surface on which it is applied and the STRESS is obtained. Viscosity is a measure of the resistance that the liquid opposes to the flow and is given by the ratio between the shear stress and the flow gradient (Pa·s). The SLIDING GRADIENT is given by the ratio between the rotation speed and the thickness of the gap.

Viscosity and Shear Rate Parameters

In particular, to characterize the gel formed after the introduction of the APS into water, two types of tests were conducted on the example of composition 1 and on the comparative composition:

1—determination of the flow curve.

Analysis parameters: shear rate 0.1-100 s−1
  Temperature 37 °C
  Number of replicas 3

2—determination of the Linear Viscoelastic Region (LVER)

Analysis parameters: shear strain 0.1-100%
  Frequency 5.0 Hz
  Temperature 37 °C
  Number of replicas 3

INSTRUMENT: ROTATIONAL REOMETER TA INSTRUMENT
GEOMETRY: PLATE-CONE C60 mm
GAP: 29 μm
TEMPERATURE: 37 °C
NUMBER OF REPLICAS: 3

3.1 Preparation of Samples:

1 L of thermostated drinking water at a temperature of 50 °C was added to a 2 L beaker. For each test, 150 ml of water at 50 °C was taken and placed in a 200 ml beaker. For each measurement, 1 sachet of granules was gradually added to the beaker and the suspension was stirred manually for 1 minute.

The time elapsed between the preparation of the gel and the measurement was 30 s. 1 ml of product was loaded onto the measuring pan.

3.2 Results:

Using the flow curve determination test, the viscosity of the sample is measured at different applied shear rates. What is obtained is a graph that shows the viscosity trend (η, Pa·s) as a function of the shear rate (γ•, s−1). As can be seen from the graph shown in FIG. 2, the behaviour of the gel formed by the APS example of composition 1 was found to be comparable to a pseudoplastic non-Newtonian fluid, i.e. a fluid characterized by a viscosity that decreases as the flow gradient increases. The composition example 1 has a lower viscosity, around 123 Pa·s, at a flow gradient of 0.1 s−1 compared to the comparison example characterized by a viscosity of about 206 Pa·s, indicating that the formation of the gel occurs more slowly and homogeneously. This results into greater ergonomics in the GI tract which allows a more homogeneous mixing with the content present in it and in a reduction of side effects, thus favouring the compliance of the product.

The determination of the Linear Viscoelastic Region (LVER-Linear Visco Elastic Region) is a measurement carried out with an oscillatory method that allows to evaluate the viscoelastic behaviour of a material by identifying the shear strain values (deformation γ*, %) for which the sample is deform. By applying to the sample a shear force of increasing intensity and with a constant frequency of oscillation, the mechanical structure of the material breaks at a given deformation. At this point, if the sample is able to flow it will begin to behave like a liquid. The parameters evaluated by this test are G' and G". G' is the elastic (or conservative) modulus and defines the ability of the material to accumulate energy in the form of elastic deformations (reversible); G" is the viscous (dissipative) modulus and defines the material's ability to dissipate energy through sliding. Within the LVER, modules G' and G" have a constant value as in this area the system does not undergo any changes since the response of the material does not depend on the stress applied to it. As shown in FIG. 3, the composition example 1 is characterized by a wider LVER than the comparison example, indicating a greater stability of the gel formed by the composition 1 to deformation stress despite the marked presence of lignin, a long chain insoluble fiber.

The oat fiber has a greater quantity of lignin, which, by its nature, should counteract the formation of the glucomannan gel (intercalating with it) and become poorly hydrated. Lignin is in fact a secondary metabolite of plants with a waterproofing action with little hydration capacity. From the observation of the samples in water, however, the formation of the gel is evident and, indeed, that the components interact to form a homogeneous system, thus showing an emerging property.

4. Tests of Fractioning of the Gel Obtained from the Contact of the Composition of the Invention with Water Product used for the test (500 g) composition example 1.

Suspension of the Composition in Water

The first phase of the process involves the hydration of the composition in water. The product example of composition 1 was hydrated in water in a ratio of about 1/50. Once in water, the product forms a gel To induce the separation of the gel, a greater quantity of water was added up to a ratio of 1/60.

From the indications obtained from the rheological study it was expected that the gel phase would naturally dissolve in a time interval greater than 2 days. The centrifuge was supposed to speed up the process. The product in suspension was hence centrifuged immediately after dissolution, but the phase remains stable, therefore it was centrifuged again after 24 hours. After waiting for 24 hours and a second spin in the centrifuge, the gel was less viscous, therefore fractionation was carried out to limit unwanted degradation phenomena. No other mechanical or thermal stress forces were applied in order not to determine a priori the breaking of the higher molecular weight fibers.

The process was carried out with a first centrifuge step for the separation of the soluble and insoluble fraction. The separation of the soluble fraction from the insoluble one was obtained after 20 minutes at 40000 rpm. The yield values relating to this fraction→insoluble fraction are shown in the general table below.

4.1 Fractionation of the Molecular Dimensions of the Components and by Affinity to Adsorbent Resins The supernatant of the centrifuge (soluble fraction) was then filtered by ultrafiltration with a spiral membrane wrapped with MWCO of 10000 Da.) The technique allows separation of the components at limited pressures through a semipermeable membrane according to their size (molecular weight).

The product with initial dilution 1/60 was still too viscous to be processed by ultrafiltration, the viscosity of the product was found to be too high resulting in fluctuating and too high membrane pressures and low permeation flows. The product was hence diluted a second time 1:2 with demineralized water (final dilution 1/120).

With this dilution it was possible to treat the whole product, although the process was slow and difficult.

At the end of the test, the membrane used is negative in the performance test, indicating an obstruction or damage to it during the process.

The retentate fraction, with a high molecular weight, was quantitatively low and in any case lower than expected. The process in general was particularly complex and high losses occurred. The low molecular weight fraction (permeate) was collected and subsequently treated on an adsorption resin column, to further characterize this fraction as a function of the affinity behaviour towards the adsorbent resins.

Difficulties were also encountered in fractionation with adsorption resin due to the residual viscosity of the fraction and the film-forming activity that determines a slow flow in the column, adhesion to the internal surfaces of the column and probably also to the porous surfaces of the resin particles. The process was consequently characterized by high process losses. The characterization of the soluble fraction is not satisfactory. Below is the table with the yields, the theoretical expected results and the results obtained from the fractionation of the APS system as per example of composition 1:

| Initial Product | Yield % compared to the initial product | Fraction characterizing the product | Theoretical expected results | Obtained results |
|---|---|---|---|---|
| Precipitate after centrifugation | 37.7 | INSOLUBLE FRACTION | Expected insoluble components of 35-40% hypothetical contribution from: opuntia, oats and stevia | The breaking phase of the gel reticulates is particularly complex: many forces have been applied: shear force under agitation and temperature, centrifugal force for prolonged periods. The soluble and insoluble fractions were separated in line with expectations, however the gel phase still present caused a large amount of losses, in fact 100% of the product is not recovered. |
| Soluble fraction | 51.1 | SOLUBLE FRACTION | | |
| | | Of which of the SOLUBLE FRACTION: | | |
| High MW fraction | 4.93 | SOLUBLE FRACTION AT HIGH MW | A yield of 25-30% was expected due to the contribution of soluble compounds with high molecular weight: deriving mainly from glucomannan and mucilage of marshmallow, lime and flax and gum Arabic | Fractionation in ultrafiltration on a wound spiral membrane was very complex as in the first test, despite the fact that the gel was not perceived, it determined a lot of resistance to the applied force with a consequent increase in the intramembrane pressure of the system and an increase in pressure. In the second fractionation test, the system was further diluted (0.5 g produced in 60 liters of water). The system behaved unexpectedly and we witnessed the passage of compounds through the membrane. |

-continued

| Initial Product | Yield % compared to the initial product | Fraction characterizing the product | Theoretical expected results | Obtained results |
|---|---|---|---|---|
| Low MW fraction | 78.0 | SOLUBLE FRACTION AT MEDIUM/LOW MW | | |
| Of which from the LOW MW FRACTION: | | | | |
| Resin Adsorbed Fraction | 11.9 | MEDIUM LOW FRACTION MW | Fraction represented by steviosylglycosides and secondary components and metabolites with antioxidant action (e.g. some low MW phenols, some low MW lignins) | The process was very complex and we assisted to a large quantative of losses |
| Fraction not adsorbed by resin | 13.1 | MEDIUM LOW FRACTION MW | Saline or sugary fraction | |

The fraction adsorbed to the resin is quantitatively high compared to the expected one, as well as the high molecular weight fraction.

The gel is therefore very stable and shows resistance to separation in its main component classes by applying physical methods.

The product, even if subjected to the physical fractionation techniques used for the separation of the various components, resists maintaining the gel structure despite the shear forces, pressure and temperature used and providing fractionation results that are not the expected based on the composition, this experimental observation allows to support again the emergent behaviour of the gel.

5. Chemical Composition of Oat Fiber and Microcrystalline Cellulose

The chemical composition of the following samples was measured:

Sample oat fiber 1

Sample oat fiber 2

Microcrystalline cellulose SF. (Chicelmi, 18H0105).

In particular, the analyses were carried out in order to determine the amount of:

- lignin;
- α-cellulose (according to a procedure that involves the determination of the intermediate holocellulose, that is, a fraction of cellulose enriched in hemicelluloses);
- hemicelluloses (obtained by difference);
- ashes.

Before carrying out the analyses, the material was sieved until reaching a particle size between 40 and 60 mesh (0.25-0.42 mm), as per convention in the case of lignocellulosic materials. The analyses were performed in duplicate.

Furthermore, before the analyses, a portion of the flour was dried in an oven at 103 °C to constant weight. In this way, the results were referred to the dry weight, as per convention. A part of this same portion was also used for the determination of the ashes.

The following other determinations were also carried out on the powder in succession:

- content of soluble extractives in organic solvents,
- content of aqueous extractives,
- acid lignin (or Klason),
- holocellulose content,
- content of α-cellulose,
- ash content.

Content of Soluble Extractives in Organic Solvents

The determination of the organic extractives content was carried out using a Soxhlet extractor in accordance with the methodology described in the TAPPI T204 standard, using a mixture of ethanol and toluene in a ratio of 1:2 as solvent.

Content of Aqueous Extractives

The determination of the aqueous extractives content was carried out in accordance with the methodology described in the TAPPI T207 standard, using the same flour already devoid of organic extractives and also in this case using a Soxhlet extractor.

Considering that the determination of both types of extractives (aqueous and organic) requires that the residue extracted from the solvents inside a flask is weighed and that the proteins are not soluble (or they are very little) neither in the organic solvents used nor nor in water, it can be considered that the value obtained in both measurements is net of the protein content of the materials analysed.

Lignin Content

The determination of lignin was carried out using the methodology described in the TAPPI T222 standard. It is commonly referred to as acid lignin or Klason. In this case, the flour already previously deprived of both organic and aqueous extractives was used. Considering that very concentrated sulphuric acid is used in the determination of lignin, that it is conceivable that the proteins dissolve completely in such an acid solution and that at the end of the procedure the insoluble residue is weighed, it can be considered that the value obtained in this measure is net of the protein content of the analysed materials.

Ash Content

The determination of the ash content was carried out in accordance with the methodology described in the TAPPI T211 standard by placing in a muffle furnace at a temperature of 525 °C for 1 hour.

Considering that all organic materials are considered degraded to the working temperature, it can be considered that the value obtained in this measure is net of the protein content of the materials analysed.

Holocellulose Content

Holocellulose is defined as all that remains of the woody material without extractives once delignified. In fact, this size corresponds to the sum of the residual cellulose and hemicelluloses, and it can therefore be determined by difference.

In particular, the holocellulose (H) was obtained through the arithmetic difference with the sum of the other chemical components.

Content of α-Cellulose

The α-cellulose content was measured directly as the residue from the holocellulose treatment with a 17.5% soda solution, according to the procedure reported in Browning (Browning, B L, 1967, Methods of wood chemistry, Vol. 1, Interscience Publishers. A Division of John Wiley and Sons Inc., New York) slightly modified (method IVALSA AC-21).

For the evaluation of α-cellulose, the holocellulose that acts as a precursor was obtained with the method of Norman and Jenkins: the extracted flour was subjected to a series of alternating treatments of acidified sodium hypochlorite and sodium sulphite, repeated until the red color due to the occurrence of the Mäule reaction disappears. It is commonly considered that α-cellulose, as a fraction of holocellulose insoluble in a strong alkaline solution, is substantially proportional to the crystalline portion of the cellulose in lignocellulosic materials.

Considering that 20% sulphuric acid is used in the procedure for the isolation of holocellulose, which it is conceivable that the proteins dissolve under these conditions, and that at the end of the procedure the insoluble residue is weighed, it can be considered that the value obtained to this extent it is net of the protein content of the materials analysed.

Hemicellulose Content

As already mentioned, the hemicelluloses were obtained by the difference between holocellulose and α-cellulose, as often suggested in the technical-scientific field2. In particular, the value is obtained by calculating the difference:

$$\text{emicellulose}=H-\alpha-\text{cellulos2}$$

Results

| | Material | | | | | |
|---|---|---|---|---|---|---|
| | Oat Fiber 1 | | Oat Fiber 2 | | Microcrystalline cellulose | |
| Sample | A1 | A2 | B1 | B2 | C1 | C2 |
| Organic extractives, % | 1.7 | 1.8 | 2.2 | 2.2 | 0.2 | 0.2 |
| Aqueous extractives, % | 2.5 | 2.6 | 3.8 | 3.9 | 0.2 | 0.3 |
| Lignine, % | 21.4 | 20.8 | 18.6 | 20.2 | 0.1 | 0.1 |
| Olocellulose, % | 68.5 | 68.9 | 69.3 | 67.7 | 99.5 | 99.4 |
| α-Cellulose, % | 40.2 | 40.6 | 40.1 | 39.6 | 9.7 | 9.4 |
| Ashes, % | 3.9 | 3.8 | 4.0 | 3.9 | 0.0 | 0.0 |
| Proteins*, % | 2.1 | 2.1 | 2.2 | 2.2 | — | — |

Composition Example 1

Statistical Methods

Quantitative data are presented as mean, standard deviation (sd), median, first and third quartile (Q1-Q3), minimum and maximum, categorical data as absolute frequency and percentage.

The BMI was calculated and classified into 4 classes.

The analyses were carried out with the SAS 9.4 software.

Check of Questionnaires

In the event that the patient at question 9 declares that the alteration is not present, no answer is expected to be present at question 10. In some cases this did not occur. If the patient answered, "It is not among the altered parameters" to question 9 and entered an answer to question 10 (it happens 20 times, in a total of 9 patients) question 10 was modified and considered empty (i.e. the symptom is not is present). In 6 out of 15 patients on question 10 were asked to answer simultaneously regarding the time of effectiveness of the example of composition 1 for controlling the increase in blood sugar or impaired glucose tolerance. If in question 9 the patient replied "It is not among the altered parameters", the corresponding variable of question 10 was left empty, otherwise the score of the compound one was considered for both variables.

Patient 1-05 to question 9 for blood pressure indicates both enough and "not among the vital signs". It was considered "Not among the vital signs".

Patient 1-03 indicated, on question 11, that he did not lose weight, but on question 12 he indicated the kg lost. The answer to question 11 was considered "yes".

In patients 1-01 to 1-05 in question 3 the weight was indicated before taking the example of composition 1, in the other patients, on the other hand, the current weight at the date of filling in the questionnaire was entered. Weight was considered for all patients when filling in the questionnaire: for patients 1-01 to 1-05 this was calculated as "initial weight"–"lost weight" using the answer to question 12.

In 3 patients, "No" was marked in question 6, but then it was indicated that something was being followed in addition to taking the example of composition 1. For these patients, "Yes" was considered as the answer.

Results

Data were collected from 15 patients, 73% (11 out of 15) female and 53% (8 out of 15) aged between 31 and 50 years, 100% (15 out of 15) overweight or obese (table 1). The current mean weight of the patients is 97.27 (sd 14.04), the mean BMI is 37.41 (sd 6.21).

In tables 1 to 6 the data are presented for the whole population.

TABLE 1

Social-demographic data

| | | Summary statistics | Total (N = 15) |
|---|---|---|---|
| Gender | Man | %, n | 26.7% (4/15) |
| | Woman | %, n | 73.3% (11/15) |
| Age | 18-30 | %, n | 13.3% (2/15) |
| | 31-50 | %, n | 53.3% (8/15) |
| | 51-64 | %, n | 26.7% (4/15) |
| | >64 | %, n | 6.7% (1/15) |
| Weight | | N | 15 (100.0%) |
| | | Mean ± SD | 97.27 ± 14.043 |
| | | Median | 99.00 |
| | | (Q1-Q3) | (92.00-108.00) |
| | | Min-Max | 66.0-123.0 |
| | | Missing | 0 |
| Height | | N | 15 (100.0%) |
| | | Mean ± SD | 1.62 ± 0.096 |
| | | Median | 1.58 |
| | | (Q1-Q3) | (1.53-1.72) |
| | | Min-Max | 1.5-1.8 |
| | | Missing | 0 |
| BMI | | N | 15 (100.0%) |
| | | Mean ± SD | 37.41 ± 6.206 |
| | | Median | 37.80 |
| | | (Q1-Q3) | (31.96-42.10) |
| | | Min-Max | 26.4-46.7 |
| | | Missing | 0 |
| BMI in classes | 25-30 | %, n | 13.3% (2/15) |
| | >30 | %, n | 86.7% (13/15) |

87% (13 out of 15) of patients takes composition example 1 from more than 3 months. 13 of 15 patients (87%) take it in addition to something else: 67% (10 of 15) also follow a diet program, 7 of 15 (47%) also follow a regular physical activity program and 7 of 15 (47%) also takes other drugs to control metabolic parameters. 5 out of 15 patients (33%) suffer from diabetes and all of these (100%, 5 out of 5) are undergoing therapy for this disease.

TABLE 2

Intake data Example of composition 1 diseases

| | | Summary statistics | Total (N = 15) |
|---|---|---|---|
| How long have you been taking Composition example 1 | More than 1 month | %, n | 13.3% (2/15) |
| | More than 3 months | %, n | 86.7% (13/15) |
| Do you take something else in addition to Composition example 1 | | %, n | 86.7% (13/15) |
| Additional weight control program | | %, n | 66.7% (10/15) |
| Additional physical activity program | | %, n | 46.7% (7/15) |
| Additional drugs | | %, n | 46.7% (7/15) |
| Diabetes | | %, n | 33.3% (5/15) |
| Therapy for diabetes | | %, n | 100.0% (5/5) |

Table 2 Intake Data Example of Composition 1 Diseases

87% of patients (13 out of 15) declared that composition example 1 was "Sufficiently" effective for controlling LDL cholesterol. Still 87% (13 out of 15) declared that it was "Sufficiently" effective for the control of triglycerides. 40% (6 out of 15) of patients declared that composition example 1 was "not very" effective for controlling HDL cholesterol. 93% (14 of 15) of the patients did not have glucose tolerance among the impaired parameters. Still 93% (14 out of 15) of the patients did not have blood pressure among the altered parameters.

TABLE 3

| How effective was Composition Example 1 in controlling alterations of each of the following metabolic parameters? | | Summary statistics | Total (N = 15) |
|---|---|---|---|
| Abdominal circumference | Scarce | %, n | 20.0% (3/15) |
| | Sufficiently | %, n | 80.0% (12/15) |
| LDL cholesterol | Scarce | %, n | 13.3% (2/15) |
| | Sufficiently | %, n | 86.7% (13/15) |
| HDL cholesterol | Scarce | %, n | 40.0% (6/15) |
| | Sufficiently | %, n | 60.0% (9/15) |
| Triglycerides | Little | %, n | 13.3% (2/15) |
| | Sufficiently | %, n | 86.7% (13/15) |
| Fasting blood sugar | Not among my symptoms | %, n | 46.7% (7/15) |
| | Scarce | %, n | 6.7% (1/15) |
| | Sufficiently | %, n | 40.0% (6/15) |
| | Very much | %, n | 6.7% (1/15) |
| Glucose tolerance | Not among my symptoms | %, n | 93.3% (14/15) |
| | Sufficiently | %, n | 6.7% (1/15) |
| Arterious pressure | Not among my symptoms | %, n | 93.3% (14/15) |
| | Scarce | %, n | 6.7% (1/15) |

8 out of 15 patients (53%) received support from the composition example 1 in the control of abdominal circumference changes after three months, while 2 out of 15 patients (13%) found no improvement. For LDL cholesterol 47% (7 out of 15) of patients were able to see benefits after three months, while for HDL cholesterol after 3 months 40% (6 out of 15) of patients had help. After 3 months, 43% (6 out of 14) of patients 10 noted an improvement in the control of triglyceride alterations. For changes in fasting blood glucose, 57% (4 out of 7) of patients saw benefits from example composition 1 after two months.

TABLE 4

| After how long from the start of taking composition example 1 was the product helpful in controlling the alterations of each of the following metabolic parameters? | | Summary statistics | Total (N = 15) |
|---|---|---|---|
| Abdominal circumference | Non ho riscontrato miglioramenti | %, n | 13.3% (2/15) |
| | After more than three months | %, n | 13.3% (2/15) |
| | After three months | %, n | 53.3% (8/15) |
| | After two months | %, n | 13.3% (2/15) |
| | After one month | %, n | 6.7% (1/15) |
| LDL cholesterol | After more than three months | %, n | 13.3% (2/15) |
| | After three months | %, n | 46.7% (7/15) |
| | After two months | %, n | 26.7% (4/15) |
| | After one month | %, n | 13.3% (2/15) |
| HDL cholesterol | After more than three months | %, n | 26.7% (4/15) |
| | After three months | %, n | 40.0% (6/15) |
| | After two months | %, n | 20.0% (3/15) |
| | After one month | %, n | 13.3% (2/15) |
| Triglycerides | After more than three months | %, n | 14.3% (2/14) |
| | After three months | %, n | 42.9% (6/14) |
| | After two months | %, n | 28.6% (4/14) |
| | After one month | %, n | 14.3% (2/14) |
| Fasting blood sugar | After more than three months | %, n | 14.3% (1/7) |
| | After three months | %, n | 14.3% (1/7) |
| | After two months | %, n | 57.1% (4/7) |
| | After one month | %, n | 14.3% (1/7) |
| Glucose tolerance | After one month | %, n | 100.0% (1/1) |

TABLE 4-continued

| After how long from the start of taking composition example 1 was the product helpful in controlling the alterations of each of the following metabolic parameters? | | Summary statistics | Total (N = 15) |
|---|---|---|---|
| Arterious pressure | After more than three months | %, n | 100.0% (1/1) |

93% (13 of 14) of the patients had a weight reduction. Patients lost an average of 3.38 kg (SD 1.2), with an average percentage change (weight lost/initial weight*100) of 3.47% (SD 1.3).

12 out of 14 patients (86%) forgot to take the composition example 1 less than 10% of the time, 15% (2 out of 13) stopped taking it for more than 2 days.

TABLE 5

| Weight reduction and interruption of composition example 1 | | Summary statistics | Total (N = 15) |
|---|---|---|---|
| Weight reduction | | %, n | 92.9% (13/14) |
| Lost weight (kgs) | | N | 13 (86.7%) |
| | | Mean ± SD | 3.38 ± 1.193 |
| | | Median (Q1-Q3) | 3.00 (2.00-4.00) |
| | | Min-Max | 2.0-5.0 |
| | | Missing | 2 |
| Starting weight | | N | 13 (86.7%) |
| | | Mean ± SD | 99.00 ± 14.595 |
| | | Median (Q1-Q3) | 100.00 (97.00-103.00) |
| | | Min-Max | 70.0-128.0 |
| | | Missing | 2 |
| Weight change from start (%) | | N | 13 (86.7%) |
| | | Mean ± SD | 3.47 ± 1.289 |
| | | Median (Q1-Q3) | 3.41 (2.53-4.00) |
| | | Min-Max | 1.9-5.7 |
| | | Missing | 2 |
| Forgot to take | Less than 10% of the times | %, n | 85.7% (12/14) |
| | Between 10% and 20% | %, n | 14.3% (2/14) |
| Interrupted intake | | %, n | 15.4% (2/13) |

50% of patients (7 out of 14) declared that with the example of composition 1 the quality of their life is "quite" improved. In 6 out of 9 patients (67%) we have an improvement in mood, no patient reports an improvement in social life, performance at work or attention in daily actions. 89% of patients (%) declare that composition example 1 can avoid the use of drugs to control metabolic parameters if combined with a diet program and a regular physical activity program. 56% (5 out of 9) consider the safety of composition example 1 "excellent", 44% (4 out of 9) "good".

TABLE 6

Life and safety improvement of Composition example 1

| | | Summary statistics | Total (N = 15) |
|---|---|---|---|
| Quality of life improvement with Composition example 1 | Not at all | %, n | 21.4% (3/14) |
| | Little | %, n | 28.6% (4/14) |
| | Sufficiently | %, n | 50.0% (7/14) |
| Mood improvement | | %, n | 66.7% (6/9) |
| Social life improvement | | %, n | 0.0% (0/9) |
| Work improvement | | %, n | 0.0% (0/9) |
| Sleep improvement | | %, n | 11.1% (1/9) |
| Attention improvement | | %, n | 0.0% (0/9) |
| Fatigue improvement | | %, n | 22.2% (2/9) |
| Composition example 1 avoids the use of drugs | Yes, but combined with a diet plan + regular physical activity program | %, n | 88.9% (8/9) |
| | Yes, but combined with at least a diet plan | %, n | 11.1% (1/9) |
| Safety | Good | %, n | 44.4% (4/9) |
| | Excellent | %, n | 55.6% (5/9) |

The same tests were also carried out for the composition examples 2, 3, 4 and 5, for which results comparable to those reported in tables 1-6 relating to composition example 1 were obtained.

The invention claimed is:

1. A method of treating metabolic syndrome, comprising administering to a subject in need thereof a therapeutically effective amount of a mixture comprising from 56% to 84% w/w of dietary fibers, wherein from 31% to 47% w/w of said mixture is represented by soluble fibers and from 25% to 37% w/w of said mixture is represented by insoluble fibers; vegetable fats from 0.28% to 0.42% w/w; vegetable phenols from 0.08% to 0.16% w/w; vegetable terpenes from 0.52% to 0.78% w/w; vegetable sugars from 1.62% to 2.70% w/w; water from 6.2% to 9.3%; inorganic compounds of vegetable origin, from 3.6% to 5.7% w/w; nitrogenous substances of vegetable origin from 1.84% to 2.76% w/w.

2. The method of treating metabolic syndrome of claim 1, wherein said mixture is administered in the appropriate dosage before main meals.

3. The method of treating metabolic syndrome of claim 2, wherein said mixture is administered at a dosage of 1.5 to 2.5 g before each main meal.

4. The method of treating metabolic syndrome according to claim 1, wherein said dietary fibers are from 59.7% to 80.8% w/w of vegetable fibers, wherein from 33.2% to 45% w/w of said mixture is represented by soluble fibers and from 26.5% to 35.8% w/w of said mixture is represented by insoluble fibers or wherein said dietary fibers are from 63% to 77% w/w of vegetable fibers, wherein from 35% to 43% w/w of said mixture is represented by soluble fibers and from 28% to 34% w/w of said mixture is represented by insoluble fibers.

5. The method of treating metabolic syndrome according to claim 1, wherein at least the 30% of said dietary insoluble fibers is α-cellulose and at least the 15% of said dietary insoluble fibers is lignin or wherein at least the 35% of said dietary insoluble fibers is α-cellulose and at least the 17% of said dietary insoluble fibers is lignin, or wherein at least the 40% of said dietary insoluble fibers is α-cellulose and at least the 18% of said dietary insoluble fibers is lignin.

6. The method of treating metabolic syndrome according to claim 1, wherein said dietary fibers are at least two of: dietary fibers of hemp, cotton, bamboo, konjac, glucomannan, oat, spelt, rice, corn, wheat, barley, baobab, carrot, opuntia, daikon, citrus albedo, *stevia*, linden, linen, althea, mallow, acacia, xanthan gum, Larch, *Cyamopsis tetragonoloba*, sterculia, *ceratonia*, topinambur, pea, soy, *psyllium*, dandelion, chicory, amaranth, agave, karkadè, Aloe vera, inulin, Arabic gum and are present inside said mixture in the form of flours, powders and/or aqueous or hydroalcoholic extracts.

7. The method of treating metabolic syndrome according to claim 6, wherein said dietary fibers comprise fibers of glucomannan, oat, opuntia, *stevia*, inulin and Arabic gum.

8. The method of treating metabolic syndrome according to claim 1, wherein the mixture is comprised in a composition, the composition comprising the mixture and at least one pharmaceutically acceptable or food grade excipient and/or carrier and/or natural flavor, wherein said mixture constitutes the active principle of said composition.

9. The method of treating metabolic syndrome according to claim 1, wherein the mixture is in the form of granulate or tablet.

10. The method of treating metabolic syndrome of claim 8, wherein said composition is administered in the appropriate dosage before the main meals.

11. The method of treating metabolic syndrome of claim 10, wherein said composition is administered at a dosage of 1.5 to 2.5 g before each main meal.

12. The method of treating metabolic syndrome according to claim 8, wherein the composition is in the form of granulate, tablet, or capsule.

* * * * *